United States Patent [19]

Teulon

[11] 4,005,103
[45] Jan. 25, 1977

[54] PYRROLIDINE DERIVATIVES

[75] Inventor: Jean-Marie Teulon, La Celle St-Cloud, France

[73] Assignee: Societe Anonyme dite: Hexachimie, Rueil-Malmaison, France

[22] Filed: Sept. 11, 1974

[21] Appl. No.: 505,084

[30] Foreign Application Priority Data

Sept. 27, 1973 United Kingdom ............ 45395/73

[52] U.S. Cl. ............. 260/326.5 CA; 260/326.5 D; 260/326.5 R; 260/326.8; 260/340.5; 260/590 C; 424/274

[51] Int. Cl.² ..................................... C07D 207/08

[58] Field of Search .......... 260/326.5 CA, 326.5 R, 260/326.8, 326.5 D

[56] References Cited

UNITED STATES PATENTS 3,135,766  6/1964  Gould ......................... 260/326.5 R
3,452,015  6/1969  Dillard et al. .............. 260/326.8 X

OTHER PUBLICATIONS

Chem. Abs., 1970, vol. 72, pp. 430 and 431.

Primary Examiner—Dale R. Ore
Attorney, Agent, or Firm—Bacon & Thomas

[57] ABSTRACT

The invention provides compounds of formula

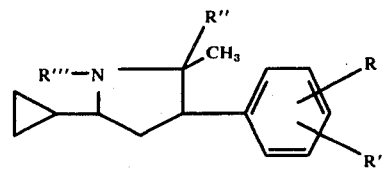

wherein R and R' are hydrogen, halogen, alkyl, alkoxy, trihalomethyl or hydroxy or they together form methylenedioxy, R" is hydrogen or methyl, and R''' is hydrogen, alkyl, benzyl, propargyl or hydroxyethyl, or salts thereof. The compounds are useful as anorexigenic or analeptic agents.

21 Claims, No Drawings

PYRROLIDINE DERIVATIVES

THIS invention relates to new compounds which are cyclopropyl phenylpyrrolidine derivatives, to a process for their preparation, to pharmaceutical compositions containing them, and to a method of using them.

The compounds of the invention have the general formula (I)

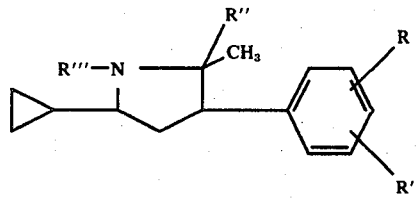

wherein each of the groups R and R', which may be the same or different, is a hydrogen or halogen atom, a lower alkyl or alkoxy group, a trihalomethyl (especially trifluoromethyl) group or hydroxy group, and can be in the meta- or para-position; or R and R', taken together, can represent a methylenedioxy group; R'' is a hydrogen atom or a methyl group; and R''' is a hydrogen atom, a lower akyl group or a benzyl, propargyl or hydroxyethyl group, or a non-toxic pharmaceutically acceptable salt thereof (for example a hydrochloride, malonate and succinate). The terms "lower alkyl" and "lower alkoxy" refer to groups having 1 to 4 carbon atoms.

The compounds of the invention possess useful pharmacological activities; they can be used in therapy, especially as anorexigenic and analeptic agents.

The compounds of general formula (I) wherein R''' is H (i.e. the secondary amines) can be prepared by hydrogenation of nitropentanones of general formula (II) wherein R, R' and R'' are defined as above.

The compounds of general formula (I) wherein R''' is other than a hydrogen atom (i.e., the tertiary amines) can be prepared either by reacting a compound of general formula (I) wherein R''' is a hydrogen atom with an acid halide, corresponding to R''', followed by reduction of the amide so obtained, or by reacting a compound of general formula R'''X wherein X is a halogen.

The salts can be prepared by reaction of the appropriate acid with the base.

The nitropentanones of general formula (II) can be prepared by reacting, under the conditions of the Michael addition in a basic medium [such as triethylamine, sodium hydroxide, potassium hydroxide, quaternary ammonium hydroxide, resins which exchange OH⁻ ions (e.g. sodium or potassium alcoholates)] of nitroethane (R'' is hydrogen) or nitropropane (R'' is methyl) with a cyclopropyl styryl ketone of general formula (III) wherein R and R' are defined as above, in an organic solvent such as tetrahydrofuran, dioxan or an alcohol (preferably methanol, ethanol or isopropanol).

The cyclopropyl styryl ketones of general formula (III) can be prepared by reacting, under the conditions of the Claisen-Schmidt condensation, an aromatic aldehyde of general formula (IV) wherein R and R' are defined as above, with cyclopropyl methyl ketone in the presence of a base.

The above reactions are shown below

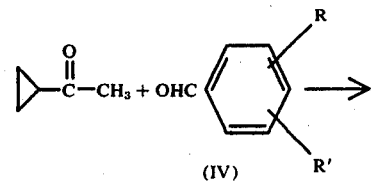

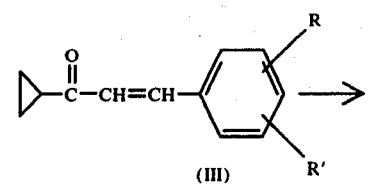

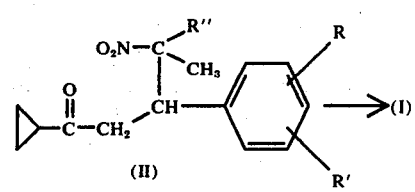

In addition, the invention provides a compound of general formula (V)

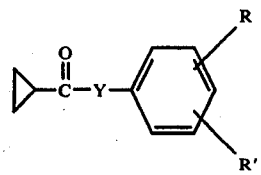

wherein R and R' are as defined above, and Y is —CH=CH—, or CH$_2$ —CH —C(NO$_2$)(CH$_3$)(R''') wherein R''' is as defined above. These compounds are useful as intermediates in the preparation of the compounds of general formula (I).

The invention also provides a pharmaceutical composition comprising a compound of general formula (I) or a salt thereof, and a pharmaceutically acceptable carrier or diluent.

The invention is illustrated by the following Examples.

EXAMPLE I

28 G (0.33 mol) of cyclopropyl methyl ketone and 46.4 g (0.33 mol) of p-chlorobenzaldehyde in 105 ml of ethanol and 170 ml of water containing 18 g of sodium hydroxide are stirred at ambient temperature for 12 hours.

The reagents are destroyed with ice and neutralised with dilute hydrochloric acid and the precipitate which forms is filtered off, washed with water and then dried and recrystallised from hexane to give 52.5 g of 1-cyclopropyl-3-(p-chlorophenyl)prop-2-en-1-one as white crystals, melting point = 61° C.

EXAMPLE II

The procedure of Example I using 46.4 g (0.33 mol) of m-chlorobenzaldehyde gives 60.9 g of 1-cyclopropyl-3-(m-chlorophenyl)prop-2-en-1-one as a liquid, after extraction with ether and distillation. Boiling point 0.1 = 130°–140° C.

EXAMPLE III

The procedure of Example I using 57.75 g (0.33 mol) of 3,4-dichloro-benzaldehyde gives 64.4 g of 1-cyclopropyl-3-(3',4'-dichlorophenyl)prop-2-en-1-one as white crystals, melting point = 74°–76° C.

EXAMPLE IV

The procedure of Example I using 40.9 g (0.33 mol) of m-fluorobenzaldehyde gives 48 g of 1-cyclopropyl-3-(m-fluorophenyl)prop-2-en-1-one as a liquid, after extraction with ether and distillation. Boiling point $_{0.1}$ = 120°–122° C.

EXAMPLE V

The procedure of Example I using 57.4 g (0.33 mol) of m-trifluoromethylbenzaldehyde gives 67.4 g of 1-cyclopropyl-3-(m-trifluoromethylphenyl)prop-2-en-1-one as a liquid, after extraction with ether and distillation. Boiling point $_{0.4}$ = 145°–150° C.

EXAMPLE VI

The procedure of Example I using 54.8 g (0.33 mol) of 3,4-dimethoxy-benzaldehyde gives 61.7 g of 1-cyclopropyl-3-(3',4'-dimethoxyphenyl)prop-2-en-1-one as white crystals, after recrystallisation from isopropanol. Melting point = 89°–91° C.

EXAMPLE VII

The procedure of Example I using 49.5 g (0.33 mol) of piperonal gives 53 g of 1-cyclopropyl-3-(3',4'-methylenedioxyphenyl)prop-2-en-1-one as white crystals, after recrystallisation from isopropyl ether, melting point = 83°–85° C.

EXAMPLE VIII

The procedure of Example I using 39.6 g (0.33 mol) of p-methylbenzaldehyde gives 49 g of 1-cyclopropyl-3-(p-methylphenyl)prop-2-en-1-one as white crystals, melting point = 75°–76° C.

EXAMPLE IX 22.5 G of 1-cyclopropyl-3-phenylprop-2-en-1-one and 12 ml of nitroethane in 130 ml of methanol containing sodium methylate prepared from 1.6 g of sodium is refluxed for 12 hours. After cooling, the reagents are destroyed with water-ice, neutralised with dilute hydrochloric acid and extracted with ether; the ether extract is washed with water and dried over sodium sulphate. The ether is evaporated in vacuo to give 19 g of 1-cyclopropyl-3-phenyl-4-nitropentanone which is used in the crude form for the remainder of the operations.

EXAMPLE X

The procedure of Example IX using 20.6 g of 1-cyclopropyl-3-(p-chlorophenyl)prop-2-en-1-one, 10 ml of nitropropane and 1.25 g of sodium in 80 ml of methanol gives 15.3 g of 1-cyclopropyl-3-(p-chlorophenyl)-4-methyl-4-nitropentanone as white crystals, after recrystallisation from ethanol. Melting point = 98°–100° C.

EXAMPLE XI

The procedure of Example IX using 24.3 g of 1-cyclopropyl-3-(p-chlorophenyl)prop-2-en-1-one, 11 ml of nitroethane and 1.5 g of sodium in 120 ml of methanol, gives 25 g of 1-cyclopropyl-3-(p-chlorophenyl)-4-nitropentanone as an oily residue which is used in the crude state for the remainder of the operations.

EXAMPLE XII

The procedure of Example IX using 33 g of 1-cyclopropyl-3-(m-chlorophenyl)prop-2-en-1-one, 15 ml of nitroethane and 2 g of sodium in 150 ml of methanol, gives 33.5 g of 1-cyclopropyl-3-(m-chlorophenyl)-4-nitropentanone as an oily residue which is used in the crude state for the remainder of the operations.

EXAMPLE XIII

The procedure of Example IX using 32.4 g of 1-cyclopropyl-3-(m-chlorophenyl)prop-2-en-1-one, 16 ml of nitropropane and 2 g of sodium in 150 ml of methanol, gives 33.3 g of 1-cyclopropyl-3-(m-chlorophenyl)-4-methyl-4-nitropentanone as an oily residue which is used in the crude state for the remainder of the operations.

EXAMPLE XIV

The procedure of Example IX using 39 g of 1-cyclopropyl-3-(3',4'-dichlorophenyl)prop-2-en-1-one, 15.5 ml of nitroethane and 2 g of sodium in 150 ml of methanol gives 41 g of 1-cyclopropyl-3-(3',4'-dichlorophenyl)-4-nitropentanone as an oily residue which is used in the crude state for the remainder of the operations.

EXAMPLE XV

The procedure of Example IX using 35.2 g of 1-cyclopropyl-3-(m-fluorophenyl)prop-2-en-1-one, 19 ml of nitropropane and 2.3 g of sodium in 180 ml of methanol gives 34.4 g of 1-cyclopropyl-3-(m-fluorophenyl)-4-methyl-4-nitropentanone as an oily residue which is used in the crude state for the remainder of the operations.

EXAMPLE XVI

The procedure of Example IX using 36 g of 1-cyclopropyl-3-(m-trifluoromethylphenyl)prop-2-en-1-one, 14 ml of nitroethane and 1.85 g of sodium in 150 ml of methanol gives 36 g of 1-cyclopropyl-3-(m-trifluoromethylphenyl)-4-nitropentanone as an oily residue which is used in the crude state for the remainder of the operations.

EXAMPLE XVII

The procedure of Example IX using 49 g of 1-cyclopropyl-3-(m-trifluoromethylphenyl)prop-2-en-1-one, 21.5 ml of nitropropane and 2.6 g of sodium in 210 ml of methanol gives 31 g of 1-cyclopropyl-3-(m-trifluoromethylphenyl)-4-methyl-4-nitropentanone as white crystals, after recrystallisation from isopropanol - pentane (50:50). Melting point 68°–70° C.

EXAMPLE XVIII

The procedure of Example IX using 21 g of 1-cyclopropyl-3-(3',4'-dimethoxyphenyl)prop-2-en-1-one, 8 ml of nitroethane and 1.2 g of sodium in 80 ml of methanol gives 16 g of 1-cyclopropyl-3-(3',4'-dimethoxyphenyl)-4-nitropentanone, which is used in the crude state for the remainder of the operations.

EXAMPLE XIX

The procedure of Example IX using 23.5 g of 1-cyclopropyl-3-(3',4'-methylenedioxyphenyl)prop-2- en-1-one, 12 ml of nitroethane and 1.4 g of sodium in 80 ml of methanol gives 20 g of 1-cyclopropyl-3-(3',4'-methylenedioxyphenyl)-4-methyl-4-nitropentanone as white crystals, after recrystallisation from isopropanol — heptane (50:50). Melting point = 70°–75° C.

EXAMPLE XX

The procedure of Example IX using 32.1 g of 1-cyclopropyl-3-(p-methylphenyl)prop-2-en-1-one, 16.5 ml of nitroethane and 2.1 g of sodium in 170 ml of methanol gives 32 g of 1-cyclopropyl-3-(p-methylphenyl)-4-nitropentanone which is used in the crude state for the remainder of the operations.

EXAMPLE XXI 15.2 G of 1-cyclopropyl-3-(p-chlorophenyl)-4-methyl-4-nitropentanone in 250 ml of methanol are hydrogenated for 7 hours 30 minutes under 100 atmospheres at 120° C in the presence of 10 g of Raney Nickel. Filtration, evaporation of the methanolic filtrate under reduced pressure and recrystallisation from isopropanol give 9 g of 2-cyclopropyl-4-phenyl-5,5-dimethyl-pyrrolidine hydrochloride as white crystals. Melting point = 271°–273° C.

EXAMPLE XXII

19 G of 1-cyclopropyl-3-phenyl-4-nitropentanone in 200 ml of methanol are hydrogenated for 7 hours 30 minutes under 100 atmospheres at 120° C in the presence of 8 g of Raney Nickel. After filtration and concentration of the filtrate in vacuo, the residue is diluted with ether and the base is neutralised with hydrogen chloride in ether. The precipitate obtained is filtered off, washed with ether and recrystallised from isopropanol to give 11 g of 2-cyclopropyl-4-phenyl-5-methyl-pyrrolidine hydrochloride as white crystals. Melting point = 190°–192° C.

EXAMPLE XXIII 15.3 G of 1-cyclopropyl-3-(p-chlorophenyl)-4-methyl-4-nitropentanone in 200 ml of ethanol saturated with ammonia are hydrogenated for 7 hours 30 minutes under 100 atmospheres at 120° C in the presence of 8 g of Raney Nickel. After filtration and concentration of the filtrate in vacuo, the residue is diluted with ethanol-ether (50:50) and the base is neutralised with hydrogen chloride in ether. The precipitate so obtained is filtered off, washed with ether and recrystallized from isopropanol to give 9.5 g of 2-cyclopropyl-4-(p-chlorophenyl)-5,5-dimethyl-pyrrolidine hydrochloride as white crystals. Melting point = 235°–240° C.

EXAMPLE XXIV

The procedure of Example XXIII using 25 g of 1-cyclopropyl-3-(p-chlorophenyl)-4-nitropentanone gives 11 g of 2-cyclopropyl-4-(p-chlorophenyl)-5-methylpyrrolidine hydrochloride as white crystals, after recrystallisation from isopropanol. Melting point = 170°–171° C.

EXAMPLE XXV

The procedure of Example XXIII using 33.5 g of 1-cyclopropyl-3-(m-chlorophenyl)-4-nitropentanone gives 15 g of 2-cyclopropyl-4-(m-chlorophenyl)-5-methylpyrrolidine hydrochloride as white crystals, after recrystallisation from isopropanol. Melting point = 191° C.

EXAMPLE XXVI

The procedure of Example XXIII using 33.3 g of 1-cyclopropyl-3-(m-chlorophenyl)-4-methyl-4-nitropentanone gives 11 g of 2-cyclopropyl-4-(m-chlorophenyl)-5,5-dimethylpyrrolidine hydrochloride as white crystals, after recrystallisation from ethyl acetate - ethanol (70:30). Melting point = 195°–200° C.

EXAMPLE XXVII

The procedure of Example XXIII using 41 g of 1-cyclopropyl-3-(3',4'-dichlorophenyl)-4-nitropentanone gives 25.6 g of 2-cyclopropyl-4-(3',4'-dichlorophenyl)-5-methylpyrrolidine hydrochloride as white crystals, after recrystallisation from isopropanol. Melting point = 214°–216° C.

EXAMPLE XXVIII

The procedure of Example XXIII using 34.4 g of 1-cyclopropyl-3-(m-fluorophenyl)-4-methyl-4-nitropentanone gives 11.8 g of 2-cyclopropyl-4-(m-fluorophenyl)-5,5-dimethylpyrrolidine hydrochloride as white crystals, after recrystallisation from isopropanol. Melting point = 220° C.

EXAMPLE XXIX

The procedure of Example XXIII using 44 g of 1-cyclopropyl-3-(m-trifluoromethylphenyl)-4-nitropentanone gives 28 g of 2-cyclopropyl-4-(m-trifluoromethylphenyl)-5-methyl-pyrrolidine hydrochloride as white crystals, after recrystallisation from ethyl acetate - isopropanol (70:30). Melting point = 176°–180° C.

EXAMPLE XXX

The procedure of Example XXII using 31 g of 1-cyclopropyl-3-(m-trifluoromethylphenyl)-4-methyl-4-nitropentanone gives 26.8 g of 2-cyclopropyl-4-(m-trifluoromethylphenyl)-5,5-dimethylpyrrolidine hydrochloride as white crystals, after recrystallisation from isopropanol. Melting point = 208°–210° C.

EXAMPLE XXXI

The procedure of Example XXII using 16 g of 1-cyclopropyl-3-(3',4'-dimethoxyphenyl)-4-nitropentanone gives 8.7 g of 2-cyclopropyl-4-(3',4'-dimethoxyphenyl)-5-methylpyrrolidine hydrochloride as white crystals, after recrystallisation from isopropanol. Melting point = 198°–200° C.

EXAMPLE XXXII

The procedure of Example XXII using 20 g of 1-cyclopropyl-3-(3',4'-methylenedioxyphenyl)-4-methyl-4-nitropentanone gives 13.8 g of 2-cyclopropyl-4-(3',4'-methylenedioxyphenyl)-5,5-dimethylpyrrolidine hydrochloride as white crystals, after recrystallisation from isopropanol. Melting point = 220°–225° C.

EXAMPLE XXXIII

The procedure of Example XXII using 32 g of 1-cyclopropyl-3-(p-methylphenyl)-4-nitropentanone gives 15.5 g of 2-cyclopropyl-4-(p-methylphenyl)-5-methyl-pyrrolidine hydrochloride as white crystals, after recrystallisation from isopropanol. Melting point = 136° C.

EXAMPLE XXXIV

5 G of 2-cyclopropyl-4-(3',4'-dichlorophenyl)-5-methylpyrrolidine are refluxed for 2½ hours in 20 ml of benzyl chloride containing 5 g of dry potassium carbonate. The reaction mixture is then taken up in ether, washed with water and dried over potassium carbonate. After the ether has been evaporated, the residue is diluted with a little ethyl acetate and the base is neutralised by adding hydrogen chloride in ether. The precipitate formed is filtered off and washed with ether to give, after recrystallisation from isopropanol, 2 g of N-benzyl-2-cyclopropyl-4-(3',4'-dichlorophenyl)-5-methylpyrrolidine hydrochloride as white crystals. Melting point = 225°–227° C.

EXAMPLE XXXV 14.6 G (0.054 mol) of 2-cyclopropyl-4-(3',4'-dichlorophenyl)-5-methylpyrrolidine and 6.5 g of propargyl bromide (0.054 mol) in 50 ml of hexamethylphosphorotriamide is stirred at ambient temperature for 2 hours in the presence of 6 g of sodium bicarbonate. The reaction mixture is heated at 70° C for 1 hour and then cooled. Ice is added and the organic products are extracted with ether; the ether extract is washed with water and dried over sodium carbonate. The ether is evaporated in vacuo and the residue is diluted with ethyl acetate and the base is neutralised by adding hydrogen chloride in ether. The precipitate formed is filtered off and washed with ether to give, after recrystallisation from isopropanol, 7.5 g of N-propargyl-2-cyclopropyl-4-(3',4'-dichlorophenyl)-5-methylpyrrolidine hydrochloride as white crystals. Melting point = 178° C.

EXAMPLE XXXVI

The procedure of Example XXXV using 12.7 g (0.054 mol) of 2-cyclopropyl-4-(p-chlorophenyl)-5-methylpyrrolidine gives 6 g of N-propargyl-2-cyclopropyl-4-(p-chlorophenyl)-5-methylpyrrolidine hydrochloride as white crystals, after recrystallisation from isopropanol. Melting point = 173°–177° C.

EXAMPLE XXXVII

The procedure of Example XXXV using 15 g of 2-cyclopropyl-4-(p-chlorophenyl)-5-methyl-pyrrolidine and 8.8 g of bromoethanol gives 6.6 g of N-hydroxyethyl-2-cyclopropyl-4-(p-chlorophenyl)-5-methylpyrrolidine hydrochloride as white crystals after recrystallisation from ethyl acetate — acetone (50:50). Melting point = 175°–180° C.

EXAMPLE XXXVIII

13 G of 2-cyclopropyl-4-(m-trifluoromethylphenyl)-5-methylpyrrolidine, 6 ml of acetyl chloride and 8 ml of triethylamine in 50 ml of anhydrous benzene is stirred at ambient temperature for 18 hours. Ice is added to the reaction mixture and the organic products are extracted with ether; the ethereal extract is washed with water, with 5% sodium hydroxide and then again with water, and dried over sodium carbonate to give 14.4 g of N-acetyl-2-cyclopropyl-4-(m-trifluoromethylphenyl)-5-methylpyrrolidine, which is dissolved in 50 ml of anhydrous tetrahydrofuran and added dropwise to a suspension of 2.9 g of lithium aluminium hydride in 75 ml of anhydrous tetrahydrofuran at reflux temperature. Refluxing is then continued for 4 hours. The excess double hydride is destroyed with cold ethyl acetate. After adding water and ice, the mixture is extracted with ether; the ethereal extract is washed with water and dried over sodium carbonate. After evaporation of the ether, vacuum distillation of the residue gives 9.7 g of N-ethyl-2-cyclopropyl-4-(m-trifluoromethylphenyl)-5-methylpyrrolidine as a liquid. Boiling point $_{0.3}$ = 115° C.

The pharmacological activities of the compounds of the invention are illustrated below.

1. POTENTIATION OF AMPHETAMINE

The test compound is administered intraperitoneally to rats 30 minutes before the intraperitoneal injection of 5 mg/kg of d-amphetamine sulphate. The intensity of the stereotypies over a period of 3 hours is assessed by attributing a number from 0 to 4. Table I indicates the sum of the assessments as a function of the doses administered. The maximum assessment is 24.

2. ANOREXIGENIC ACTIVITY IN DOGS

Beagle dogs are conditioned to take their food over the course of 5 minutes once per day. The test compound is administered orally in the form of a single dose of 10 mg/kg one hour before the food is presented. The amount of food ingested is measured at regular intervals.

TABLE I

| mg/kg Intraperitoneal administration | Compound of Example No. | | | | | | | | |
|---|---|---|---|---|---|---|---|---|---|
| | XXI | XXII | XXIII | XXIV | XXV | XXVI | XXVII | XVIII | XXIX |
| 0 | 6 | 8 | 8 | 8 | 7 | 7 | 12 | 7 | 8 |
| 0.5 | — | — | — | — | 13 | — | — | — | — |
| 1 | — | 8 | — | 7 | — | 12 | 21 | 16 | 17 |
| 2 | — | — | 12 | — | 18 | — | — | — | — |
| 4 | 10 | 9 | — | 22 | — | 14 | 23 | 17 | 22 |
| 8 | 11 | — | 18 | — | 23 | — | — | — | — |
| 16 | 13 | 12 | — | 24 | — | 19 | 24 | 16 | 16 |
| 32 | — | — | 17 | — | — | — | — | — | — |

| mg/kg Intraperitoneal administration | Compound of Example No. | | | | | | | | |
|---|---|---|---|---|---|---|---|---|---|
| | XXX | XXXI | XXXII | XXXIII | XXXIV | XXXV | XXXVI | XXXVII | XXXVIII |
| 0 | 10 | 8 | 8 | 7 | 3 | 6 | 11 | 10 | 10 |
| 0.5 | — | — | — | — | — | — | — | — | — |
| 1 | 20 | — | — | — | — | 18 | — | — | 20 |
| 2 | — | 10 | 18 | 12 | 20 | — | — | 12 | — |
| 4 | 24 | — | — | — | — | 23 | — | — | 24 |
| 8 | — | 24 | 24 | 19 | 21 | — | 24 | — | 24 |

TABLE I-continued

| 16 | 24 | — | — | — | 23 | — | 24 | — |
| 32 | — | 23 | 23 | 24 | 15 | — | 24 | 24 | — |

Table II gives the percentage inhibition of consuming food as a function of the time after treatment.

3. ANOREXIGENIC ACTIVITY IN RATS

Two batches of three Sprague Dawley male rats (130 – 180 g) are conditioned to take their daily food over the course of 7 hours. Water is given as desired. The test compound is administered orally 30 minutes before the food is presented. The amount ingested is measured 1 hour and 2 hours later. The 50% inhibiting dose in relation to the consumption of food ($ED_{50}$) and the confidence range are calculated according to the Litchfield and Wilcoxon method.

Table III gives the percentage inhibition in relation to the consumption of food as a function of the doses administered.

TABLE II

| Time | Compound of Example No. XXI | XXII | XXIII | XXIV | XXV | XXVI | XXVII | XXVIII | XXIX |
| --- | --- | --- | --- | --- | --- | --- | --- | --- | --- |
| 1 hr | 100 | 50 | 100 | 100 | 50 | 60 | 100 | 100 | 0 |
| 2 hrs | 100 | 50 | 100 | 100 | 50 | 60 | 100 | 100 | 0 |
| 4 hrs | 70 | 0 | 100 | 100 | 50 | 60 | 100 | 100 | — |
| 24 hrs | 0 | — | 50 | 80 | 0 | 0 | 100 | 0 | — |
| 48 hrs | — | — | — | 50 | — | — | 100 | — | — |

| Time | Compound of Example No. XXX | XXXI | XXXII | XXXIII | XXXIV | XXXV | XXXVI | XXXVII | XXXVIII |
| --- | --- | --- | --- | --- | --- | --- | --- | --- | --- |
| 1 hr | 0 | 0 | 100 | 0 | 100 | 60 | 0 | 0 | 0 |
| 2 hrs | 0 | 0 | 100 | 0 | 100 | 60 | 0 | 0 | 0 |
| 4 hrs | — | — | 100 | — | 100 | 60 | — | — | — |
| 24 hrs | — | — | 0 | — | 50 | 0 | — | — | — |
| 48 hrs | — | — | — | — | 0 | — | — | — | — |

TABLE III

| Dose administered mg/kg oral administration | Compound of Example XXIV | | Compound of Example XXVII | |
| --- | --- | --- | --- | --- |
| | 1 hr | 2 hrs | 1 hr | 2 hrs |
| 0.5 | — | — | 25 | 30 |
| 1 | 6 | 5 | 39 | 36 |
| 2 | 44 | 53 | 28 | 37 |
| 4 | 47 | 34 | 58 | 55 |
| 8 | 77 | 71 | 84 | 83 |
| 16 | 77 | 80 | 100 | 100 |
| $ED_{50}$ mg/kg oral administration | 3.5 (1.20–10.1) | 5.6 (2.8–11.2) | 2.3 | 2.2 |

TABLE IV

| Dose administered mg/kg oral administration | Isolated mice | | |
| --- | --- | --- | --- |
| | Compound of Example XXIV | Compound of Example XXVII | Amphetamine |
| 16 | 0 | 0 | 0 |
| 32 | 0 | 20 | 0 |
| 64 | 0 | 70 | 10 |
| 128 | 27 | — | 100 |

4. TOXICITY

Batches of 10 mice are placed in boxes covered with grids (20 × 10 × 10 cm), either isolated individually, or in groups of 10. The test compound is administered orally to them. The death rate is noted 4 hours after the treatment.

Tables IV and V below give the percentage death rate for the products of Examples XXIV and XXVII compared with d-amphetamine sulphate.

TABLE V

| Dose administered mg/kg oral administration | Mice in groups | | |
| --- | --- | --- | --- |
| | Compound of Example XXIV | Compound of Example XXVII | Amphetamine |
| 4 | — | — | 0 |
| 8 | — | — | 20 |
| 16 | 0 | 0 | 100 |
| 32 | 0 | 0 | 100 |
| 64 | 0 | 0 | — |
| 128 | 0 | 70 | — |

5. CARDIOVASCULAR ACTIVITY

When amphetamine is injected intravenously into anaesthetised dogs, it causes pulmonary and systemic hypertension. The compounds of Examples XXIV and XXVII do not cause these phenomena but, in contrast, cause systemic hypotension.

6. CLINICAL ACTIVITY

When the compounds of Examples XXIV and XXVII are administered to man at a daily dose of 50 mg, they result in a decrease in the amount of food ingested daily. The compounds are preferably presented in a form suitable for oral administration, for example in the form of gelatin-coated pills containing 25 mg of the active ingredient.

The compounds of the present invention possess anorexigenic properties which are at least equivalent to those of amphetamine, both in animals and in man, without having the side effects of amphetamine on behaviour and arterial pressure.

We claim:

1. A compound of formula

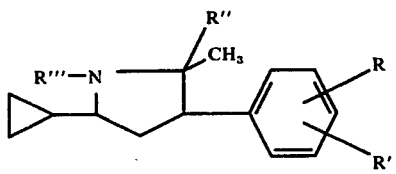

wherein each of the groups R and R', which may be the same or different is a hydrogen or halogen atom, a lower alkyl or alkoxy group, or a trihalomethyl or hydroxy group, the groups R and R' being in the meta- or para-position, or R and R', taken together, is a methylenedioxy group, R'' is a hydrogen atom or a methyl group, and R''' is a hydrogen atom or a lower alkyl, benzyl, propargyl or hydroxyethyl group, or a non-toxic pharmaceutically acceptable salt thereof.

2. A compound as claimed in claim 1, wherein at least one of R or R' is a trifluoromethyl group.

3. A compound as claimed in claim 1 in the form of the hydrochloride.

4. A compound as claimed in claim 1 and which is 2-cyclopropyl-4-(p-chlorophenyl)-5-methyl-pyrrolidine or a non-toxic pharmaceutically acceptable salt thereof.

5. A compound as claimed in claim 1 and which is 2-cyclopropyl-4--(3',4'-dichlorophenyl)-5-methylpyrrolidine or a non-toxic pharmaceutically acceptable salt thereof.

6. A compound as claimed in claim 1 and which is 2-cyclopropyl-4-phenyl-5,5-dimethylpyrrolidine or a non-toxic pharmaceutically acceptable salt thereof.

7. A compound as claimed in claim 1 and which is 2-cyclopropyl-4-phenyl-5-methylpyrrolidine or a non-toxic pharmaceutically acceptable salt thereof.

8. A compound as claimed in claim 1 and which is 2-cyclopropyl-4-(p-chlorophenyl)-5,5-dimethylpyrrolidine or a non-toxic pharmaceutically acceptable salt thereof.

9. A compound as claimed in claim 1 and which is 2-cyclopropyl-4-(m-chlorophenyl)-5-methylpyrrolidine or a non-toxic pharmaceutically acceptable salt thereof.

10. A compound as claimed in claim 1 and which is 2-cyclopropyl-4-(m-chlorophenyl)-5,5-dimethylpyrrolidine or a non-toxic pharmaceutically acceptable salt thereof.

11. A compound as claimed in claim 1 and which is 2-cyclopropyl-4-(m-fluorophenyl)-5,5-dimethylpyrrolidine or a non-toxic pharmaceutically acceptable salt thereof.

12. A compound as claimed in claim 1 and which is 2-cyclopropyl-4-(m-trifluoromethylphenyl)-5-methylpyrrolidine or a non-toxic pharmaceutically acceptable salt thereof.

13. A compound as claimed in claim 1 and which is 2-cyclopropyl-4-(m-trifluoromethylphenyl)-5,5-dimethylpyrrolidine or a non-toxic pharmaceutically acceptable salt thereof.

14. A compound as claimed in claim 1 and which is 2-cyclopropyl-4(3',4'-dimethoxyphenyl)-5-methylpyrrolidine or a non-toxic pharmaceutically acceptable salt thereof.

15. A compound as claimed in claim 1 and which is 2-cyclopropyl-4-(3',4'-methylenedioxyphenyl)-5,5-dimethylpyrrolidine or a non-toxic pharmaceutically acceptable salt thereof.

16. A compound as claimed in claim 1 and which is 2-cyclopropyl-4-(p-methylphenyl)-5-methylpyrrolidine or a non-toxic pharmaceutically acceptable salt thereof.

17. A compound as claimed in cliam 1 and which is N-benzyl-2-cyclopropyl-4-(3', 4'-dichlorophenyl)-5-methylpyrrolidine or a non-toxic pharmaceutically acceptable salt thereof.

18. A compound as claimed in claim 1 and which is N-propargyl-2-cyclopropyl-4-(3',4'-dichlorophenyl)-5-methylpyrrolidine or a non-toxic pharmaceutically acceptable salt thereof.

19. A compound as claimed in claim 1 and which is N-propargyl-2-cyclopropyl-4-(p-chlorophenyl)-5-methylpyrrolidine or a non-toxic pharmaceutically acceptable salt thereof.

20. A compound as claimed in claim 1 and which is N-hydroxyethyl-2-cyclopropyl-4-(p-chlorophenyl)-5-methylpyrrolidine or a non-toxic pharmaceutically acceptable salt thereof.

21. A compound as claimed in claim 1 and which is N-ethyl-2-cyclopropyl-4-(m-trifluoromethylphenyl)-5-methylpyrrolidine or a non-toxic pharmaceutically acceptable salt thereof.

* * * * *